(12) United States Patent
Andreacchi (10) Patent No.: US 7,357,854 B1
(45) Date of Patent: Apr. 15, 2008

(54) PROCESS FOR ELECTROPOLISHING A DEVICE MADE FROM COBALT-CHROMIUM

(75) Inventor: Anthony S. Andreacchi, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 938 days.

(21) Appl. No.: 10/223,273

(22) Filed: Aug. 19, 2002

(51) Int. Cl.
   *C25F 3/16* (2006.01)
(52) U.S. Cl. ............ 205/674; 205/640; 205/682; 205/684; 205/723
(58) Field of Classification Search ........ 205/640–686, 205/723
   See application file for complete search history.

(56) References Cited

U.S. PATENT DOCUMENTS

| | | | |
|---|---|---|---|
| 2,645,611 A * | 7/1953 | Axtell | 205/671 |
| 2,674,571 A * | 4/1954 | Prosen | 205/678 |
| 3,556,883 A | 1/1971 | Naito et al. | |
| 3,986,970 A | 10/1976 | Shiga | |
| 4,425,204 A * | 1/1984 | McLaughlin | 205/671 |
| 5,158,548 A | 10/1992 | Lau et al. | |
| 5,344,425 A | 9/1994 | Sawyer | |
| 5,421,955 A | 6/1995 | Lau et al. | |
| 5,449,372 A | 9/1995 | Schmaltz et al. | |
| 5,514,154 A | 5/1996 | Lau et al. | |
| 5,679,470 A | 10/1997 | Mayer | |
| 5,750,434 A | 5/1998 | Urushidani et al. | |
| 5,824,077 A | 10/1998 | Mayer | |
| 5,891,191 A | 4/1999 | Stinson | |
| 6,019,784 A | 2/2000 | Hines | |
| 6,131,266 A | 10/2000 | Saunders | |
| 6,334,871 B1 | 1/2002 | Dor et al. | |
| 6,355,058 B1 | 3/2002 | Pacetti et al. | |

(Continued)

FOREIGN PATENT DOCUMENTS

JP         56152999 A   * 11/1981

(Continued)

OTHER PUBLICATIONS

*Standard Guide for Electrolytic Polishing of Metallographic Specimens*, American Society and Materials (Designation: E 1558-93), pp. 1-12, 1993, n.m.

(Continued)

*Primary Examiner*—Susy Tsang-Foster
*Assistant Examiner*—Nicholas A. Smith
(74) *Attorney, Agent, or Firm*—Fulwider Patton LLP (57) ABSTRACT

The invention is directed to an electropolishing solution for products or devices made from at least in part a cobalt-chromium alloy. The invention is particularly suitable for medical devices or intravascular stents made at least in part of cobalt-chromium. More particularly, the electropolishing process of the invention is particularly suited for use on implantable medical devices, such as stents, due to the biocompatibility of cobalt-chromium alloys. The invention is directed to an improved stent formed from a cobalt-chromium alloy, that possesses an ultrasmooth shiny surface. This invention is also directed to a method of electropolishing such a stent using an acidic electrolytic solution comprising a mixture of 6 parts of about 98% sulfuric acid ($H_2SO_4$), 1 part of about 37% hydrochloric acid (HCl) and 1 part by of about 85% concentrated phosphoric acid ($H_3PO_4$) to produce an exceptionally smooth surface.

16 Claims, 3 Drawing Sheets

U.S. PATENT DOCUMENTS 6,465,124 B1 * 10/2002 Medeiros et al. ........... 429/105
6,736,952 B2 * 5/2004 Emesh et al. ................. 205/81
6,916,409 B1 * 7/2005 Callol et al. ........... 204/297.05

FOREIGN PATENT DOCUMENTS

JP 409207029 A * 8/1997

OTHER PUBLICATIONS

*Standard Practice for Microetching Metals and Alloys,* American Society and Materials (Designation: E 407-93), pp. 1-18, 1993, n.m.
*Standard Test Method for Macroetching Metals and Alloys,* American Society and Materials (Designation: E 340-93), pp. 1-10, 1993, n.m.
Surman, Hartmut et al., Automatic Electropolishing of Cobalt Chromium Dental Cast Alloys With A Fuzzy Logic Controller, *Computers Chemical Engineering,* vol. 22, No. 7-8, pp. 1099-1111, 1998, n.m.
ESMA, Inc. Brochure re electropolishers; Mar. 2002.
*Standard Guide for Electrolytic Polishing of Metallographic Specimens,* American Society and Materials (Designation: E 1558-93), pp. 1-12, 1993.
*Standard Practice for Microetching Metals and Alloys,* American Society and Materials (Designation: E 407-93), pp. 1-18, 1993.
*Standard Test Method for Macroetching Metals and Alloys,* American Society and Materials (Designation: E 340-93), pp. 1-10, 1993.
Surman, Hartmut et al., Automatic Electropolishing of Cobalt Chromium Dental Cast Alloys With a Fuzzy Logic Controller, *Computers Chemical Engineering,* vol. 22, No. 7-8, pp. 1099-1111, 1998.

* cited by examiner

PROCESS FOR ELECTROPOLISHING A DEVICE MADE FROM COBALT-CHROMIUM

BACKGROUND OF THE INVENTION

The invention relates generally to providing an electrolytic acid solution for electropolishing products made from cobalt-chromium alloys. More particularly, the invention relates to electropolishing medical devices made of cobalt-chromium alloys, and even more particularly, the invention relates to electrolytic acid solutions used to smoothly electropolish stents formed from cobalt-chromium alloy. This invention includes the solutions, the method of electropolishing a cobalt-chromium stent using the solutions, and a cobalt-chromium stent having an outer surface electropolished with the solutions.

While a wide range of products or devices can be made from a cobalt-chromium alloy for use with the present invention, medical devices are particularly suitable due to the biocompatible characteristics of cobalt-chromium products. Thus, for example, implantable medical devices or devices that are used within the human body are particularly suitable and can be made from a cobalt-chromium alloy that has been electropolished in accordance with the present invention. More particularly, and as described in more detail herein, intravascular stents can be made from a cobalt-chromium alloy that has been electropolished according to the invention. Thus, while the description of prior art devices and of the invention herein refers mainly to intravascular stents, the invention is not so limited.

Stents are generally metallic tube shaped intravascular devices which are placed within a blood vessel to structurally hold open the vessel. The device can be used to maintain the patency of a blood vessel immediately after intravascular treatments and can be used to reduce the likelihood of development of restenosis. Expandable stents are frequently used as they may travel in compressed form to the stenotic site generally either crimped onto an inflation balloon or compressed into a containment sheath in a known manner.

Expandable stents formed from metal offer a number of advantages and are widely used. Metallic serpentine stents, for example, not only provide strength and rigidity once implanted they also are designed sufficiently compressible and flexible for traveling through the tortuous pathways of the vessel route prior to arrival at the stenotic site. Additionally, metallic stents may be radiopaque, thus easily visible by radiation illumination techniques such as x-ray film.

It is highly desirable for the surface of the stent to be extremely smooth so that it can be inserted easily and experience low-friction travel through the tortuous vessel pathway prior to implantation. A roughened outer surface may result in increased frictional obstruction during insertion and excess drag during travel to the stenotic site as well as damaging the endothelium lining the vessel wall. A rough surface may cause frictional resistance to such an extent as to prevent travel to desired distal locations. A rough finish may also cause damage to the underlying inflation balloon. A less rough finish decreases thrombogenicity and increases corrosion resistance.

Stents have been formed from various metals including stainless steel, tantalum, titanium, platinum, nickel-titanium which is commonly called nitinol, and alloys formed with cobalt and chromium. Stainless steel has been extensively used to form stents and has often been the material of choice for stent construction. Stainless steel is corrosion resistant, strong, yet may be cut into very thin walled stent patterns.

Cobalt-chromium alloy is a metal that has proven advantages when used in stent applications. Stents made from cobalt-chromium alloy may be thinner and lighter in weight than stents made from other metallic materials, including stainless steel. Cobalt-chromium alloy is also a denser metal than stainless steel. Additionally, cobalt-chromium stents are nontranslucent to certain electromagnetic radiation waves, such as X rays, and, relative to stainless steel stents, provide a higher degree of radiopacity, thus being easier to identify in the body under fluoroscopy.

Metal stents, however, suffer from a number of disadvantages. They often require processing to eliminate undesirable burrs, nicks, or sharp ends. Expandable metal stents are frequently formed by use of a laser to cut a framework design from a tube of metal. The tubular stent wall is formed into a lattice arrangement consisting of metal struts with gaps therebetween. Laser cutting, however, typically is at high temperature and often leaves debris and slag material attached to the stent. Such material, if left on a stent, would render the stent unacceptable for implantation. Treatment to remove the slag, burrs, and nicks is therefore required to provide a device suitable for use in a body lumen.

Descaling is typically a first treatment of the surface in preparation for further surface treatment such as electropolishing. Descaling may include, for example, scraping the stent with a diamond file, followed by dipping the stent in hydrochloric acid or a hydrochloric acid mixture, and thereafter cleaning the stent ultrasonically. A successfully descaled metal stent should be substantially slag-free in preparation for subsequent electropolishing.

Further finishing is often accomplished by the well known technique of electropolishing. Grinding, vibration, and tumbling techniques are often not suited to be employed on small detailed parts such as stents.

Prior art electropolishing methods generally improve the smoothness of the metal surface, but as applied to cobalt-chromium stents have had been limited in the ability to produce a desirably consistent smooth surface.

Electropolishing is an electrochemical process by which surface metal is dissolved. Sometimes referred to as "reverse plating," the electropolishing process actually removes metal from the surface desired to be smoothed. The metal stent is connected to a power supply (the anode) and is immersed in a liquid electrolytic solution along with a metal cathode connected to the negative terminal of the power supply. Current is applied and flows from the stent, causing it to become polarized. The applied current is controlled to control the rate at which the metal ions of the anodic stent are generally removed and diffused through the solution to the cathode.

The rate of the electrochemical reaction is proportional to the current density. The positioning and thickness of the cathode in relation to the stent is important to make available an even distribution of current to the desired portion of the stent sought to be smoothed.

The straightforward application of current, however, does not necessarily translate to even distribution of current across the entire surface sought to be polished. One important feature to creating an even surface on the desired portion of the part is the formation of current differential during the electropolishing process across the surface. Electropolishing provides varied current density to the surface imperfections such as undulations creating protrusions and valleys on the surface. Current density is highest at high points on the surface and lowest at the low points. The increased current density at the raised points causes the metal to dissolve faster at these points thus leveling the surface while forming a corrosion-inhibiting oxide layer.

Electropolishing in the proper electrolytic solution, can serve to smooth out the exposed rough surface to the point where it is ultrasmooth, shiny, and reflective. However, traditional methods have not proved effective to consistently produce an ultrasmooth, shiny finish on a stent comprised of cobalt-chromium alloy.

Treated with traditional electrolytic or etching solutions, such as those specified in ASTM E407-93, ASTM E340-95, and ASTM E1558-93, a stent formed of cobalt-chromium alloy may reveal a variety of finishes ranging from a rather rough and unfinished appearance, a matte finish which is pitted, brown, blackened, feathered, etched, dimpled, rough, and/or uneven.

One prior art electropolishing solution, comprising about 3 parts by volume of about 98% concentrated sulfuric acid and 1 part by volume of about 37% hydrochloric acid (hereinafter referred to as the "3:1" solution), provided an improved surface finish for cobalt-chromium stents. A suitable overall treatment for a cobalt-chromium stent using the 3:1 prior art electropolishing solution includes initial descaling wherein the stents are dipped in a hydrochloric acid solution and thereafter ultrasonically cleaned, electropolishing using the prior art 3:1 solution and then some final electropolishing using a mildly acidic solution. The above treatment produces an acceptable surface finish for a cobalt-chromium stent having a tubular wall with a wall thickness, before surface treatment, of about 0.005 inch. However, it has a tendency to produce an uneven, pitted surface on cobalt-chromium stents having a tubular wall with a wall thickness, before surface treatment, of about 0.004 inch. Heretofore, there has been no effective method to consistently produce an ultrasmooth, shiny finish on the surface of a cobalt-chromium stent with a wall thickness, before surface treatment, of about 0.004 inch.

It would be desirable to provide an electropolishing solution which would acceptably polish stents with wall thicknesses of 0.004 inch as well as up to 0.005 inch. A stent having a 0.004 inch thick tubular wall may be preferable when smaller final dimensions for wall thickness are desired. Also, a stent having a 0.004 inch thick tubular wall will generally have a shorter process time and more uniformity across the length of the stent.

It would also be desirable to provide an electropolishing solution that could acceptably polish a cobalt-chromium stent without an initial descaling treatment or without final electropolishing using a different solution in order to reduce process time and the number of different solutions needed. Further, it would be desirable to provide an electropolishing solution with an increased threshold for both metal ion and water contamination in order to reduce the frequency of changing the solution, thus further reducing process time and costs.

What is needed is a process for treating a product or device made of a cobalt-chromium alloy to consistently produce an ultrasmooth surface as well as to provide a more simplified process, including a reduction in process time, the number of solutions needed and the frequency of replacing the solution. The present invention satisfies these needs.

SUMMARY OF THE INVENTION

The invention is directed to a process of electropolishing a product or device made from a cobalt-chromium alloy. The product or device is particularly useful for medical devices such as medical implants, hip joints, bone screws, guide wires, catheters, filters, and intravascular stents. Other products and devices unrelated to the medical device products described herein also will benefit from the electropolishing solution and process when such products or devices are made from cobalt-chromium alloys. Since the electropolishing process of the invention is particularly useful for medical devices and more particularly useful for intravascular stents, the process is described herein with respect to stents, but is not so limited.

The invention is directed to an improved product or device, such as a stent, formed from a cobalt-chromium alloy, that possesses an ultrasmooth, shiny exterior surface. This invention is also directed to a method of electropolishing such a stent using an acidic electrolytic solution comprising a mixture of about 6 parts of about 98% concentrated sulfuric acid ($H_2SO_4$), about 1 part of about 37% concentrated hydrochloric acid (HCl), and about 1 part of 85% concentrated phosphoric acid ($H_3PO_4$) (hereinafter referred to as the "6:1:1 solution") to produce an exceptionally smooth surface. In another embodiment, the solution comprises a mixture of about 6 parts of about 98% concentrated sulfuric acid ($H_2SO_4$) and about 1 part of 85% concentrated phosphoric acid ($H_3PO_4$) to produce an exceptionally smooth surface. In yet another embodiment, the acidic electrolytic solution comprises about 1 part by volume of a first component selected from the group consisting of ethylene glycol, ethylene glycol derivatives and mixtures thereof and at least about 2 parts by volume of a second component that is an acid (hereinafter referred to as the "ethylene glycol solution") to produce a smooth and shiny surface. More particularly, solutions of this embodiment may comprise about 1 part by volume of the first component that is a mixture of about equal parts by volume of ethylene glycol, ethylene glycol bisthioglycolate and ethylene glycol diacetate and either about 3 parts by volume of the second component that is about 98% concentrated sulfuric acid or about 6 parts by volume of the second component that is a mixture of about 5 parts by volume of 98% concentrated sulfuric acid and about 1 part by volume of 37% hydrochloric acid or 85% phosphoric acid.

Compared to stainless steel, cobalt-chromium alloy provides a strong, flexible, lower weight and higher density stent. Cobalt-chromium alloy also provides a greater degree of radiopacity than stainless steel, a very desirable property when seeking to locate the stent and when attempting to observe its performance once implanted in a vessel, such as a peripheral vessel or coronary artery.

The ability to consistently and adequately finish the surface of a cobalt-chromium stent has, however, been limited. The improved method of finishing a stent comprised of cobalt-chromium alloy herein disclosed provides an ultrasmooth, shiny, stent surface suitable for low-friction insertion and travel to the luminal location.

In the present invention, to achieve an ultrasmooth, bright and shiny surface of a cobalt-chromium stent, the composition of the electrolytic solution is an important criteria. It has been determined that one embodiment which achieves such a result is comprised of a solution of about 6 parts of about 98% concentrated sulfuric acid ($H_2SO_4$), about 1 part of about 37% concentrated hydrochloric acid (HCl) and about 1 part of 85% concentrated phosphoric acid ($H_3PO_4$). The solution may also include an ethylene glycol mixture as a component. Another embodiment which achieves a smooth and shiny surface is a solution comprising about 1 part by volume of a first component that is a mixture of about equal parts by volume of ethylene glycol, ethylene glycol bisthioglycolate and ethylene glycol diacetate and either about 3 parts by volume of a second component that is about 98% concentrated sulfuric acid or about 6 parts by volume of a second component that is a mixture of about 5 parts by volume of 98% concentrated sulfuric acid and about 1 part by volume of 37% hydrochloric acid or 85% phosphoric acid. The concentration of acids may vary according to a particular smoothness requirement. The time that the cobalt-chromium product or stent is exposed to the solution, the temperature of the solution and the current (ranging from about 1 amp to about 5 amps) also are factors that impact the surface finish of the cobalt-chromium stent or other product.

The 6:1:1 solution of the present invention consistently produces a stent which has an ultrasmooth and shiny exterior surface. Further, the solution produces ultrasmooth, shiny stents from hypotubes having a 0.004 inch thick tubular wall in addition to hypotubes having a 0.005 inch thick tubular wall. The 6:1:1 solution more consistently produces an acceptably polished 0.004 inch thick stent compared to the prior art 3:1 solution and provides a smoother and shinier surface finish overall than the prior art 3:1 solution on 0.004 inch thick stents. Compared to the prior art 3:1 electropolishing solution, the 6:1:1 solution of the present invention is also able to treat a cobalt-chromium stent in a shorter period of time. The 6:1:1 solution of the present invention is able to electropolish a stent in a fewer number of cycles and also eliminates the need for either an initial descaling treatment or additional electropolishing with a different, final solution, both of which were required by the prior art 3:1 solution. Furthermore, the 6:1:1 solution of the present invention is able to withstand a greater water concentration and metal ion concentration before becoming ineffective to further polish the stents.

The ethylene glycol solution of the present invention is also capable of producing a smooth and shiny stent. In particular, the surface finish obtainable from electropolishing a stent with the ethylene glycol solution eliminates the need for the final electropolishing solution.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention is directed to an electropolishing solution and product treated by that solution. More specifically, a product or device formed from at least in part a cobalt-chromium alloy, is electropolished in a solution of acid for a predetermined time and temperature in order to form an oxide coating on the product or device which provides a smooth and shiny surface. In particular, the process of the invention is particularly suitable for medical devices made of cobalt-chromium since cobalt-chromium is a biocompatible metal alloy. More particularly, implantable devices such as intravascular stents, prosthetic devices, bone screws, and the like can be made from cobalt-chromium alloys and be treated with the electropolishing solution of the present invention. While the electropolishing solution of the present invention can be used with any product or device made at least in part from cobalt-chromium to produce a smooth and shiny surface, the use of the invention for intravascular stents made from cobalt-chromium is particularly suitable and is described in much more detail herein. The invention is not limited to use with stents for medical devices.

The improved cobalt-chromium stent is formed from an alloy composed of cobalt and chromium comprising at least fifty percent by weight of the alloy and including one or more of a variety of metals and elements as is known in the art including, but not limited to nickel, titanium, tantalum, nickel-titanium, tungsten, manganese, molybdenum, silicon, carbon, and nitrogen. In one embodiment, an alloy of Co—Cr—W (cobalt-chromium-tungsten) was evaluated. Cobalt-chromium stents can be made from alloys known in the art by the tradenames Haynes®25, L605, and Stellite 25. Alternatively, the improved stent may be formed with an exterior metal surface comprised of an alloy of cobalt and chromium.

Typically, a cobalt-chromium stent incorporates a desired lattice configuration usually laser cut from a tube of cobalt-chromium alloy. During the laser cutting process, frequently much of the tube is cut away, to produce a chain of ring-like elements comprised of struts in wave-like pattern with gaps therebetween and links connecting the ring elements together to form an elongated tubular body typically between 8 mm and 40 mm long. Implanted stents have an internal diameter typically between 2 mm for small vessel stents and up to 8 mm for larger vessels. Crimpable or expandable stents in a compressed condition typically have an internal diameter in the range of just under 1 mm to about 2 mm. Before electropolishing or surface treatment, the thickness of the stent wall is usually between 0.10 mm and 0.20 mm. All of these dimensions can vary to suit a particular application.

Such precision laser cutting, however, typically is at high temperature and often leaves debris and slag material attached to the stent requiring processing to eliminate it. Such debris and excess slag often exhibits itself in the form of undesirable bulges of material, burrs, nicks, and sharp ends. The stent is typically descaled by dipping the stent in 37% concentrated hydrochloric acid (HCl) or HCl solution for approximately 5 minutes. Multiple stents may be so dipped into a test tube of HCl. In one embodiment, the stent is immersed in a solution of about 9 parts of 37% concentrated HCl to 1 part of 30% concentrated hydrogen peroxide ($H_2O_2$) at room temperature. The HCl solution can be repeatedly used until it turns dark green (from contaminants). Stents should be dipped slowly in the fresh HCl as the HC may react violently with them. In lieu of hydrochloric acid, other acids may be used to descale the stent including nitric acid ($HNO_3$), phosphoric acid ($H_3PO_4$), sulfuric acid ($H_2SO_4$), or a combination of the above-mentioned acids (i.e., HCl, HNO3, $H_3PO_4$ and $H_2SO_4$).

The descaling procedure is thereafter completed by rinsing and drying the stent. The stent is ultrasonically rinsed in water, preferably distilled water at about 58° Celsius, for about two minutes and then air dried. A procedure for preparing such a stent for implantation includes descaling and electropolishing the stent.

If examination under a microscope reveals residual slag the descaling process of acid bathing, ultrasonic rinsing, and drying should be repeated, although a stent can typically be descaled in a single five minute cycle. A successful descaling of the stent should yield slag-free stents in preparation for subsequent electropolishing. Should small spots of slag stubbornly cling to the stent, they can be electropolished away without any adverse effects and without employing further descaling cycles to remove them.

Descaling yields a roughened, but clean surface available for further finishing by the well known technique of electropolishing. Stents being relatively small and fragile are well suited to electropolishing, but not to grinding, vibration, or tumbling to attain a smooth finish.

Sometimes referred to as "reverse plating," the process of electropolishing actually removes metal from the surface desired to be smoothed. Electropolishing is an electrochemical process to smooth metal surfaces by dissolution of metal, which takes place more rapidly at high points on the metal surface. The metal stent is rendered anodic (+) and is immersed in a liquid electrolytic solution along with a metal cathode (−). Current is applied and flows from the anode, polarizing it, thus encouraging the metal ions of the stent to diffuse through the solution to the cathode.

A special feature of electropolishing is the creation of current differentials across the microscopic surface of the anode. The current density is greatest at high points on the surface and lowest at the low points. The rate of the electrochemical reaction is directly proportional to the current density so that increased current density at the raised points causes the anodic metal to dissolve faster at these points thus leveling the surface material. The smoothed surface of many metals can, with sufficient electropolishing techniques including use of the proper electrolytic solution, be made sufficiently smooth to an extent as to become shiny and reflective. The finish may also be dependent on the level of current applied, the duration of applied current, and the temperature of the electrolytic solution.

Figure 1:
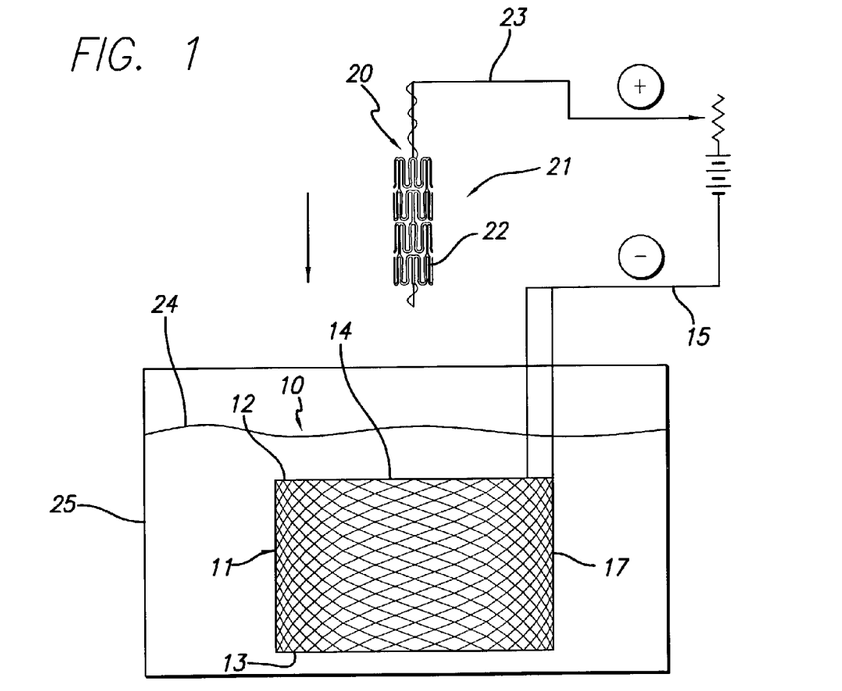
FIGS. 1 and 2 are schematic diagrams of an electropolishing fixture for use with the electropolishing procedure of present invention.
Figure 2:
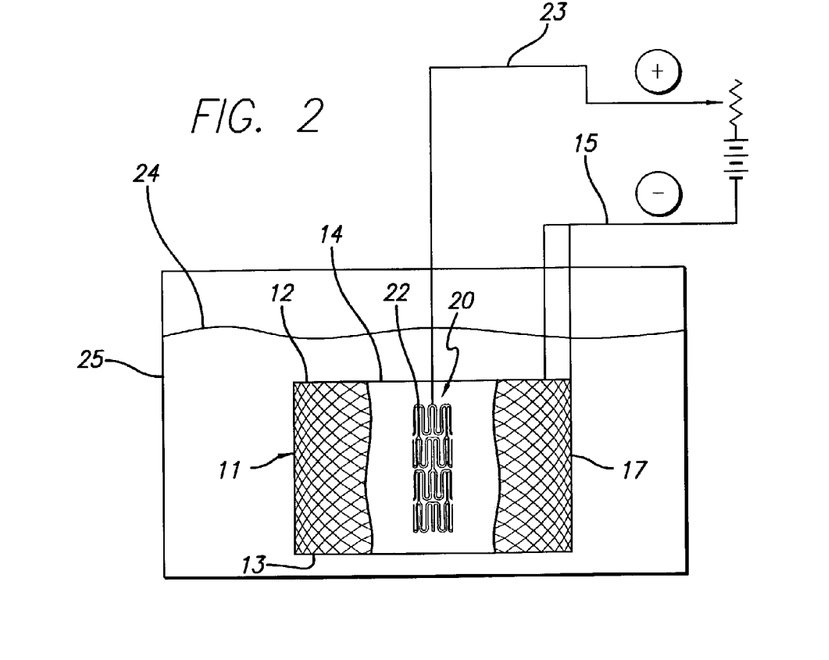

Referring to FIG. 1, a cathode 10 is provided in the form of a tubular member 11. The tubular member has a first end 12 and a second end 13, with an opening 14 extending therethrough from the first end to the second end. In one embodiment as depicted in FIGS. 1 and 2, a wire 15 is attached to a wire mesh tube 17 in which a lattice-type mesh extends substantially from the first end to the second end of the tubular member. In another embodiment, the tubular member 11 is in the form of a wire coil 16 that is generally in the shape of a helix or a spiral While the tubular member 11 of FIGS. 1 and 2 is in the form of a continuous wire mesh tube 17, the tube can be non-continuous (e.g., two or more arcuate sections with a longitudinal space between sections) and still operate as the cathode. Further, tube 17 can have other configurations such as an hour glass shape or a tapered shape to suit a particular application.

As shown in FIG. 1, an anode 20 is formed by a metallic device 21. For purposes of discussion, and by illustration only, a metallic stent 22 is depicted as forming the metallic device. A current conducting member 23 (such as a wire) is attached to one end of the metallic device in order to complete the electrical circuit between the anode and cathode. Importantly, and as shown in FIG. 2, the cathode or tubular member substantially surrounds the anode or metal device. For example, the metallic device has a length and a diameter such that the length and diameter of the tubular member is greater than the length and diameter of the metallic device. As a more specific example, a typical coronary stent 22 can range in length from approximately 6 mm to 40 mm and have an unexpanded diameter in the range of about 1.5 mm to 7 mm, depending upon the application. In order to substantially surround the metal stent, the tubular member should have a length in the range of about 10 to 60 mm and a diameter in the range of about 4 to 70 mm. Obviously, these dimensions for the metallic device and the tubular member can vary widely depending upon the application and the size of the metallic device being electropolished. Further, the invention is not limited to electropolishing medical devices, rather it is useful for any type of metallic device capable of being electropolished and requiring an ultrasmooth surface.

In order to accomplish the electropolishing process, the cathode 10 and anode 20 are submerged in an electrolytic solution. In FIG. 1, the cathode or tubular member 11 is shown submerged in an electrolytic solution 24 which is held in a container 25 that is commonly known. The anode 20 or metallic device 21 has not yet been submerged in the electrolytic solution and positioned within the tubular member. As shown in FIG. 2, the electropolishing process is commenced when the anode or metallic device is positioned within the tubular member, in this case wire mesh tube 17, by positioning the metallic device substantially within the wire mesh tube.

The stent is composed of an alloy that includes cobalt and chromium in an amount totaling at least fifty percent by weight of the alloy. This cobalt-chromium alloy is formed into a tube and laser cut to form a stent configured in a lattice arrangement consisting of metal struts with gaps therebetween as is known in the art. After the stent is formed by laser cutting, it may optionally be descaled by dipping the stent into a bath of about 9 parts of 37% concentrated hydrochloric acid (HCl) to 1 part of 30% concentrated hydrogen peroxide ($H_2O_2$) for approximately five minutes.

The descaling procedure is thereafter completed by ultrasonically rinsing the stent, preferably in distilled water, at about 58° Celsius for about two minutes and then air dried. If after examination under a microscope residual slag remains, the descaling process acid bathing, ultrasonic rinsing, and drying should be repeated. A successful stent descaling should yield slag-free stents in preparation for subsequent electropolishing.

Alternatively, the descaling procedure may be skipped and the laser-cut stent may be electropolished with the solution of the present invention as a first step.

In preparation for the electropolishing of the stent, the electrolytic solution of the present invention is prepared. While under a vented hood, and at standard conditions, 5 ml of 37% concentrated hydrochloric acid (HCl) is poured into a beaker. Then, 5 ml of 85% concentrated phosphoric acid ($H_3PO_4$) is poured into the HCl. Next, 30 ml of 98% concentrated sulfuric acid ($H_2SO_4$) is poured into the beaker. Phosphoric acid is not reactive with hydrochloric acid and thus should be added to the HCl before the sulfuric acid is added in order to prevent a violent reaction between the HCl and sulfuric acid. Once the phosphoric acid has been added to the HCl, the sulfuric acid can be slowly poured into the solution without a violent reaction. For this reason, the 6:1:1 solution of the present invention is less reactive during preparation and easier to handle than the prior art 3:1 solution which only has HCl and sulfuric acid as components. All three acids, whether individually or as a mixture, are extremely corrosive. Contact with skin or tissue, whether through liquid spill or in the form of exposure to fumes, can be severely injurious. Appropriate safety gear should be employed when handling and disposing of such acids.

As it is known that HCl has a tendency to boil off, possibly leaving a zero or negligible HCl content in a liquid mixture, this invention also contemplates a solution comprising about 6 parts of about 98% concentrated sulfuric acid ($H_2SO_4$) and about 1 part of about 85% concentrated phosphoric acid ($H_3PO_4$).

In other embodiments, the electrolytic solution contains ethylene glycol and/or ethylene glycol derivatives as a first component and an acid as a second component. In these embodiments, equal parts by volume of ethylene glycol, ethylene glycol bisthioglycolate and ethylene glycol diacetate are combined to form the first component. In one embodiment, the electrolytic solution is then prepared by pouring 30 ml of 98% concentrated sulfuric acid (the second component) into the beaker and then adding about 10 ml of the ethylene glycol mixture (the first component). In another embodiment, the electrolytic solution is prepared by pouring 5 ml of 37% concentrated hydrochloric acid into the beaker, adding 5 ml of the ethylene glycol mixture, and then adding 25 ml of 98% concentrated sulfuric acid. In yet another embodiment, the electrolytic solution is prepared by pouring 25 ml of 98% concentrated sulfuric acid into the beaker, adding 5 ml of 85% concentrated phosphoric acid and then adding 5 ml of the ethylene glycol mixture.

Forming the anode 20, the stent 22 in one embodiment is 18 mm long and is mounted on a stainless steel, titanium or other metallic mandrel, which is conductively attached to a stainless steel clip. As is known in the art, there are a wide range of stent lengths available and reference to an 18 mm long stent is for illustration only. The clip is conductively attached to a titanium rod to which the wire 23 is attached at the opposing end of the rod to the positive terminal of a controllable power supply capable of supplying one to seven amperes at up to twenty four volts DC. The amperage and voltage can vary and in one embodiment the power supply provides one to seven amperes at up to twenty one volts.

Wire 15 is attached to the negative terminal of the power supply and is terminated at the cathode 10, such cathode formed from 90% Platinum and 10% Iridium clad over a Niobium core. For use with an 18 mm long stent, for example, the cathode or tubular member 11 is about 20 to 50 mm long and 4 to 70 mm in diameter and is submerged into the acid mixture so that the tubular member is suspended substantially in the acid. In one embodiment, the tubular member is about 36 to 40 mm high (or long) about 14 to 20 mm in diameter. The anodic stent 22 is then lowered and vertically submerged into the electrolytic acid solution 24 and positioned through the tubular member so that the ends of the stent are substantially equidistant from the tubular member. The clip remains out of the solution. The power supply is thereafter energized and adjusted altering the current controller to supply four amperes of current to the solution for a period of approximately eight seconds. While the disclosed embodiment shows stent 22 submerged in a vertical orientation, it can be rotated into other orientations such as, for example, from 0° to 90° relative to vertical.

The stent 22 is then removed from the electrolytic solution 24, rinsed with water, and turned axially on the mandrel to expose the stent surface beneath the mandrel contacts to the acid. The remounted stent is then resubmerged in the solution for additional cycles of electropolishing with another rinse and another turn relative to the mandrel. For an 18 mm-long stent, generally four to seven cycles, and typically five, are employed to produce an ultrasmooth and shiny surface using the 6:1:1 solution of the present invention. Longer stents have more surface area than shorter stents and may require more time in the acid solution and optimal results for any particular size and length of stent can easily be determined. The length of time the product or stent is in the solution is proportional to the surface area being electropolished. The greater the surface area, the more time the product or stent is exposed to the solution. The stent is thereafter cleaned ultrasonically in a distilled water bath at a temperature of 58° Celsius and subsequently air dried.

The ratio of the height of the cathode to stent length can range from about 1:1 to about 8:1. At a 1:1 ratio, the stent ends are likely to be polished less than at a ratio of 8:1. The ratio of the tubular member diameter to the stent diameter can range from about 5:1 to about 10:1. Cycle times also can vary and range from 6 to 8 seconds for cobalt-chromium stents that are about 18 mm in length when a current of about four amperes is used. Alternatively, a lower current may be used over a longer cycle time. In one embodiment, a cycle lasts about 40 to 45 seconds with a current of one to two amperes.

The present invention electropolishing apparatus also optionally includes means for circulating the electropolishing solution through the stent 22 and the tubular member 11. Various devices can be used to circulate the electrolytic solution and can include, for example, a circulation pump for rotating or oscillating, a stir bar, or a re-circulation pump. It is preferred that the solution be gently moved as opposed to a vigorous movement so that it does not interfere with the electropolishing process.

The stent may optionally be further processed with additional electropolishing cycles, typically two to four, using a proprietary solution sold under the name E272 manufactured by ESMA, Inc., South Holland, Ill. It is believed that this solution is a mildly acidic solution containing glycol ethers and glycol esters. This final step may not be needed, as the stent surface is ultrasmooth and shiny following the electropolishing treatment using the solution of the present invention. However, depending on the degree of smoothness and shine required, additional processing with the final E272 electropolishing solution may be desired, particularly if the initial descaling treatment was not performed. Use of both the initial descaling treatment and final E272 electropolishing step, however, are generally not necessary to produce a highly ultrasmooth and shiny stent surface. Typically, one processing step is eliminated in the treatment of a stent using the solution of the present invention, either the initial descaling treatment or the E272 final electropolishing step.

The electropolishing procedure employing the solution of the present invention removes material from the stent surface greatly smoothening the surface. Electropolishing also provides a protective corrosion-resistant oxide layer on the stent surface.

Compared to the prior art 3:1 solution, the processing time using the 6:1:1 solution of the present invention is reduced by about half. To acceptably polish a stent having a tubular wall with a wall thickness of about 0.005 inch using the prior art 3:1 solution, about 12 to 14 electropolishing cycles were typically required, in addition to a descaling treatment consisting of a 5 minute acid bath followed by 2 minutes of ultrasonic cleaning. This required about 8-12 minutes of processing time per stent. However, the present solution can polish a stent in about 5 electropolishing cycles without any descaling treatment, for a total processing time of about 2-3 minutes.

The ethylene glycol solution of the present invention also reduces the processing time for electropolishing cobalt-chromium stents. The ethylene glycol solution produces a smooth and shiny surface finish without using the E272 final electropolishing solution. Thus, the final E272 electropolishing step may be eliminated, reducing process time and the number of different solutions needed. However, experiments testing the solutions of the present invention indicated that solutions containing a mixture of equal parts by volume of ethylene glycol, ethylene glycol bisthioglycolate and ethylene glycol diacetate as a component were able to successfully polish stents only when used within about one day after being prepared. After about a day, these solutions had difficulty carrying the 4 ampere current and were ineffective in polishing the stents. The 6:1:1 solution, on the other hand, is stable and has an indefinitely long shelf life. The 6:1:1 solution may be prepared and used at any later time to successfully polish a stent.

Figure 3A:
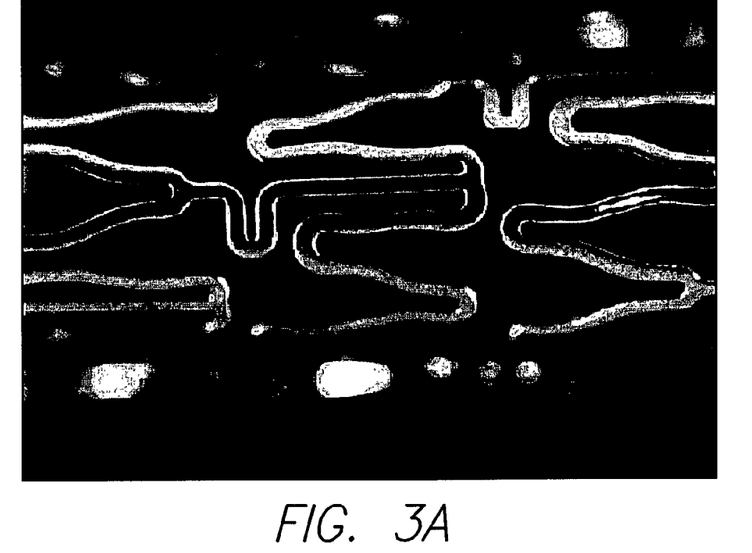
FIGS. 3A and 3B are photographs of the surface of a portion of a cobalt-chromium stent having a tubular wall with a wall thickness, before surface treatment, of about 0.004 inch electropolished with the 6:1:1 solution of the present invention.
Figure 3B:
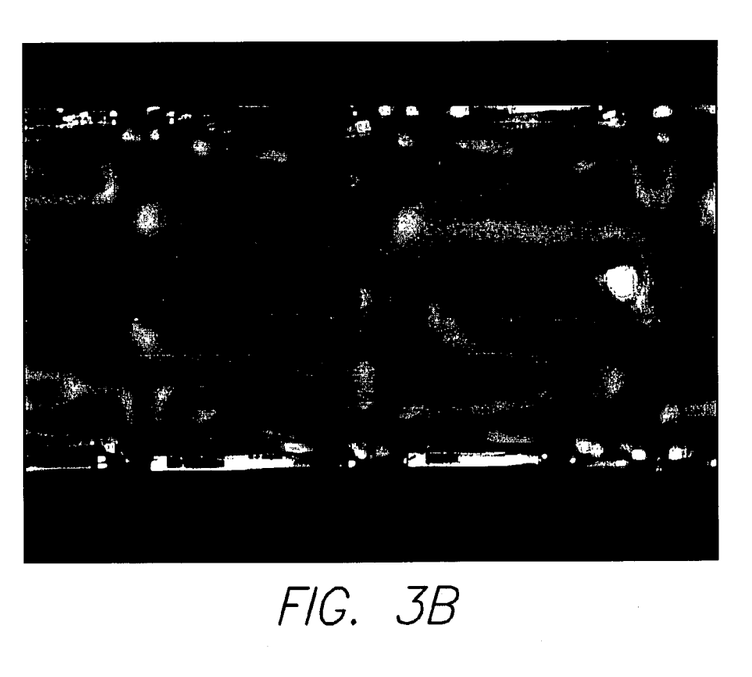

FIG. 3A illustrates, in the form of a photograph, the surface finish of an 18 mm-long cobalt-chromium stent of the present invention having a tubular wall with a wall thickness, before treatment, of about 0.004 inch and electropolished with the 6:1:1 solution of the present invention to a strut thickness at the center ring of 0.0031 inch. No descaling treatment or final E272 electropolishing step was employed. FIG. 3A reveals a surface finish that is ultrasmooth and shiny without surface defects such as pock marks or surface pits. FIG. 3B illustrates the sidewall finish of the stent in FIG. 3A. FIG. 3B reveals ultrasmooth and shiny sidewalls.

Figure 4A:
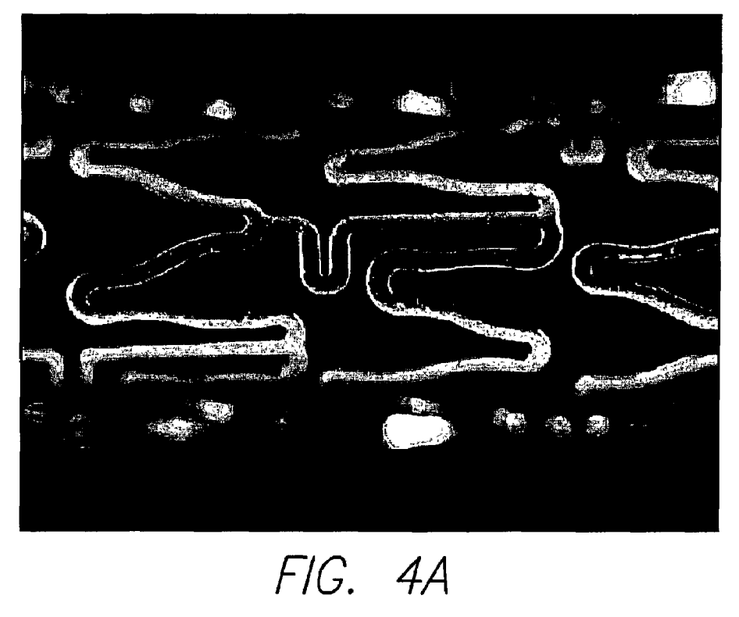
FIGS. 4A and 4B are photographs of the surface of a portion of a cobalt-chromium stent tube having a wall thickness, before surface treatment, of about 0.004 inch electropolished with a prior art solution consisting of about 3 parts of about 98% concentrated sulfuric acid to 1 part of about 37% concentrated hydrochloric acid.
Figure 4B:
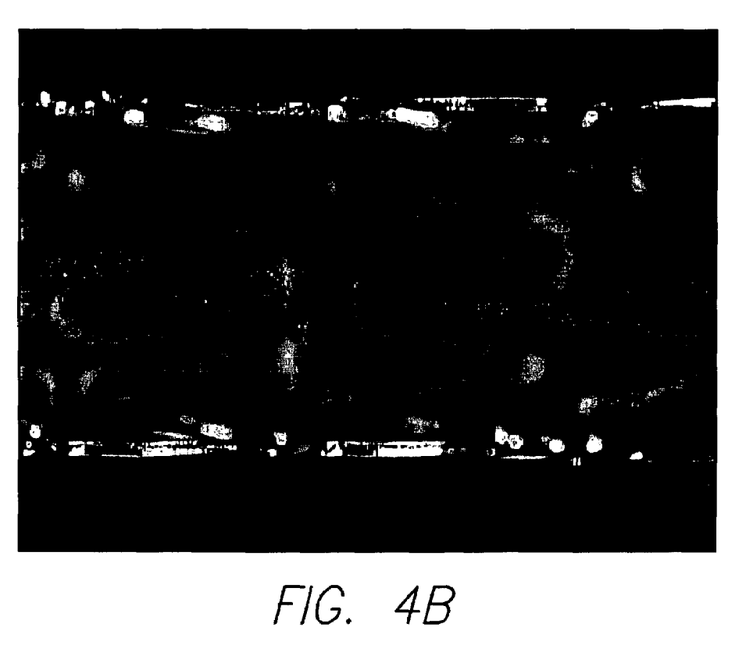

FIG. 4A illustrates, in the form of a photograph, the surface finish of an 18 mm-long cobalt-chromium stent composed from a tube having a tubular wall with a wall thickness, before treatment, of about 0.004 inch electropolished using the prior art 3:1 electrolytic solution to a strut thickness at the center ring of 0.0031 inch. No descaling treatment or final E272 electropolishing step was employed. FIG. 4A reveals surface pitting, pock marks and surface scratches that remained after electropolishing under similar test conditions and to the same center strut thickness as with the solution of the present invention. FIG. 4B illustrates the sidewall finish of the stent in FIG. 4A. FIG. 4B reveals sidewalls with some rough edges and scratches. Thus, it can be seen that use of the 6:1:1 electrolytic solution of the present invention on cobalt-chromium parts cut from 0.004 inch thick tubes produces a surface finish that is substantially smoother than that achieved by the prior art solution for the same thickness. The 6:1:1 solution of the present invention also produces an ultrasmooth and shiny finish on a stent composed from a tube having a wall thickness of about 0.005 inch.

Using a Wyko NT3300 Syrface Profiler (from Veeco Instruments, Inc., Woodbury, N.Y.), roughness average (Ra) values were measured on cobalt-chromium stents electropolished with the solutions of the present invention and with the prior art 3:1 solution. A final electropolishing step using the E272 solution was performed on the stents in these measurements. Roughness average values for stents electropolished to a target strut thickness at the center ring of 0.0032 inch using the 6:1:1 solution of the present invention were measured to be ultrasmooth at approximately 101 nm. However, to attain comparable roughness average values, stents electropolished with the prior art 3:1 solution had to be overpolished to a final strut thickness at the center ring of 0.0024 to 0.0026 inch, far outside the target thickness. Thus, experimental trials confirm that use of the electrolytic solution of the present invention on cobalt-chromium parts produces an ultrasmooth surface finish while the prior art solution is unable to achieve such a finish on 0.004 inch thick stents within the target dimensions. As a result, the prior art solution can be unacceptable for use on 0.004 inch thick stents, while the 6:1:1 solution of the present invention proves successful.

Experiments were also performed to determine the water contamination thresholds of the solutions. Water contamination was defined as the amount of water that enters the solution (by carryover, absorption, etc.) before polishing ceases and the solution needs to be exchanged. The experiments on water contamination revealed that the 3:1 prior art solution ceased to further polish stents at approximately a 2.5% water content level while the 6:1:1 solution still performed suitably with over a 10% water content level. The 6:1:1 solution, therefore, has a higher resistance to water contamination than the 3:1 prior art solution, requiring less frequent replacement.

In addition, the longevity of the 6:1:1 solution of the present invention and the prior art 3:1 solution were also studied. Longevity was defined as the total number of stents that could be acceptably polished per unit volume of solution. The ability of a solution to polish is reduced as the metal ion and water concentrations increase. Using stents with wall thicknesses before treatment of about 0.004 inch, 60 ml of the prior art 3:1 solution polished 12 stents before the solution failed, while 60 ml of the 6:1:1 solution of the present invention polished 17 stents before the solution failed. Therefore, the 6:1:1 solution of the present invention has increased longevity compared to the prior art 3:1 solution, requiring less frequent replacement.

Concentration of the acid components of the present invention may be found in convenient reagent grades of about 37% concentrated hydrochloric acid, about 98% concentrated sulfuric acid and about 85% concentrated phosphoric acid. Typically, reagent grade acids vary to some extent in concentration from the concentration depicted on the container label, usually within 3% of their stated concentration. Decreasing smoothness of the stent surface is experienced by varying the six to one to one ratio of the acids substantially in either direction.

As is the nature of many parameters of various processes, parameters of the electropolishing process may be altered by degree to provide similar results. It is the intention to include such modification, within the scope of the invention, and as is known in the art, of time, temperature, humidity, pressure, voltage, Current, cathode material, cathode dimension, degree of descaling, rinsing, as well as other variable parameters not heretofore mentioned.

The present invention satisfies a great need for an electrolytic solution to electropolish a product or device made from cobalt-chromium, such as a cobalt-chromium stent, to consistently produce an ultrasmooth surface finish, and satisfies a great need for a cobalt-chromium stent possessing such a surface. Additionally, the present invention satisfies the need for a method to electropolish a cobalt-chromium stent to such a surface finish.

The embodiments heretofore discussed are in no way intended to limit the scope of the invention. Various changes and improvements may also be made to the invention without departing from the scope thereof.

What is claimed:

1. A method of treating a cobalt-chromium device that includes electropolishing the device in an electrolytic solution, comprising:

combining about 1 part by volume of a first component selected from the group consisting of ethylene glycol, ethylene glycol derivatives and mixtures thereof and at least about 2 parts by volume of a second component that is an acid in solution selected from the group consisting of sulfuric acid, hydrochloric acid, phosphoric acid and mixtures thereof, wherein the first component is a mixture of ethylene glycol, ethylene glycol bisthioglycolate and ethylene glycol diacetate; and submerging the device in the solution.

2. The method of claim 1, wherein the solution comprises about 1 part by volume of the first component and about 3 parts by volume of the second component, the first component being a mixture of about equal parts by volume of ethylene glycol, ethylene glycol bisthioglycolate and ethylene glycol diacetate and the second component being about 98% by weight concentrated sulfuric acid.

3. The method of claim 1, wherein the solution comprises about 1 part by volume of the first component and about 6 parts by volume of the second component, the first component being a mixture of about equal parts by volume of ethylene glycol, ethylene glycol bisthioglycolate and ethylene glycol diacetate and the second component being a mixture of about 5 parts by volume of 98% by weight concentrated sulfuric acid and about 1 part by volume of 37% by weight hydrochloric acid.

4. The method of claim 1, wherein the solution comprises about 1 part by volume of the first component and about 6 parts by volume of the second component, the first component being a mixture of about equal parts by volume of ethylene glycol, ethylene glycol bisthioglycolate and ethylene glycol diacetate and the second component being a mixture of about 5 parts by volume of 98% by weight concentrated sulfuric acid and about 1 part by volume of 85% by weight phosphoric acid.

5. The method of claim 1, wherein the device is submerged in the solution for a period of time that is proportional to the surface area of the device.

6. The method of claim 1, wherein the electropolished device is a medical device.

7. The method of claim 6, wherein the medical device is a stent.

8. The method of claim 7, wherein the stent is submerged in the solution for a period of time that is proportional to the surface area of the stent.

9. A method of treating a cobalt-chromium medical device that includes electropolishing the device in an electrolytic solution, comprising:

combining about 1 part by volume of a first component selected from the group consisting of ethylene glycol, ethylene glycol derivatives and mixtures thereof and at least about 2 parts by volume of a second component that is an acid in solution, wherein the first component is a mixture of ethylene glycol, ethylene glycol bisthioglycolate and ethylene glycol diacetate; and submerging the device in the solution.

10. The method of claim 9, wherein the solution comprises about 1 part by volume of the first component and about 3 parts by volume of the second component, the first component being a mixture of about equal parts by volume of ethylene glycol, ethylene glycol bisthioglycolate and ethylene glycol diacetate and the second component being about 98% by weight concentrated sulfuric acid.

11. The method of claim 9, wherein the solution comprises about 1 part by volume of the first component and about 6 parts by volume of the second component, the first component being a mixture of about equal parts by volume of ethylene glycol, ethylene glycol bisthioglycolate and ethylene glycol diacetate and the second component being a mixture of about 5 parts by volume of 98% by weight concentrated sulfuric acid and about 1 part by volume of 37% hydrochloric acid.

12. The method of claim 9, wherein the solution comprises about 1 part by volume of the first component and about 6 parts by volume of the second component, the first component being a mixture of about equal parts by volume of ethylene glycol, ethylene glycol bisthioglycolate and ethylene glycol diacetate and the second component being a mixture of about 5 parts by volume of 98% by weight concentrated sulfuric acid and about 1 part by volume of 85% by weight phosphoric acid.

13. The method of claim 9, wherein the device is submerged in the solution for a period of time that is proportional to the surface area of the device.

14. The method of claim 9, wherein the device is submerged in the solution for a period of time that is proportional to the surface area of the device.

15. The method of claim 9, wherein the medical device is a stent.

16. The method of claim 8, wherein the stent is submerged in the solution for a period of time that is proportional to the surface area of the stent.

* * * * *